(12) United States Patent
Kao et al.

(10) Patent No.: US 6,221,058 B1
(45) Date of Patent: Apr. 24, 2001

(54) STRUCTURE FOR INFUSION CATHETER NEEDLE

(76) Inventors: Wang-Hsiang Kao; Kuei-Chun Chen, both of P.O. Box No. 6-57, Chung-Ho City, Taipei Hsien 235 (TW)

( * ) Notice: Subject to any disclaimer, the term of this patent is extended or adjusted under 35 U.S.C. 154(b) by 0 days.

(21) Appl. No.: 09/495,377

(22) Filed: Feb. 1, 2000

(51) Int. Cl.[7] .................................................. A61M 5/00
(52) U.S. Cl. .......................................... 604/263; 604/198
(58) Field of Search .................................. 604/192, 198, 604/110, 263, 162, 272

(56) References Cited

U.S. PATENT DOCUMENTS

| | | |
|---|---|---|
| 4,762,516 | * 8/1988 | Luther et al. . |
| 5,466,223 | * 11/1995 | Bressler et al. . |
| 5,520,654 | * 5/1996 | Whalberg . |
| 5,562,624 | * 10/1996 | Righi et al. . |
| 5,833,670 | * 11/1998 | Dillon et al. . |

* cited by examiner

*Primary Examiner*—Sharon Kennedy
*Assistant Examiner*—Catherine Serke
(74) *Attorney, Agent, or Firm*—Dougherty & Troxell

(57) ABSTRACT

An improved structure of infusion catheter needle, comprised of a infusion soft needle, a steel needle protection, a steel needle and a steel needle chute; within, the chute is a long narrow casing provided with a catch above and an opening below, a catch is provided each on the external side close to where above the opening; a barrel to connect air exchange and blood back-flow mechanism is provided at a steel needle base in the chute; a square eyelet is each provided at both sides to the base to penetrate into the catch part of the chute for the base to move within the chute and engage the catch; a rubber plug provided at the tip of a one end in cone shape of the needle protection is inserted into the needle tube to secure the steel needle therein while the other end of the needle protection is provided with a joint to be inserted into the catch part, and a square eyelet corresponding to that from the base is each provided on both sides of the joint; so that after use, the steel needle is secured by the catch part and the needle is received in the protection to prevent the medical personnel from accidental needlestick injury which may lead to HIV, hepatitis B and C, and to ensure the disposal safety.

1 Claim, 4 Drawing Sheets

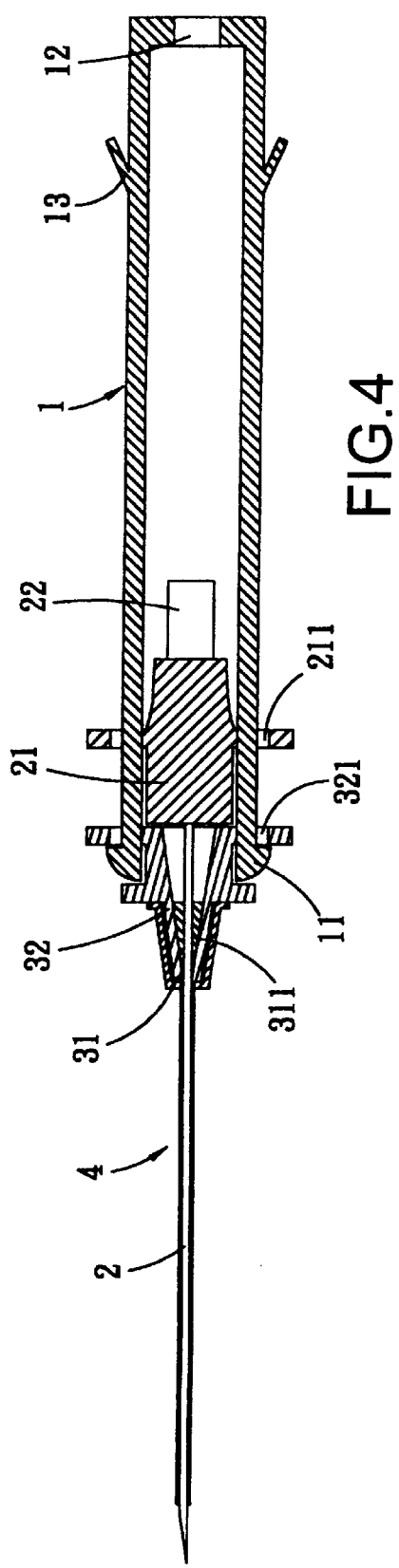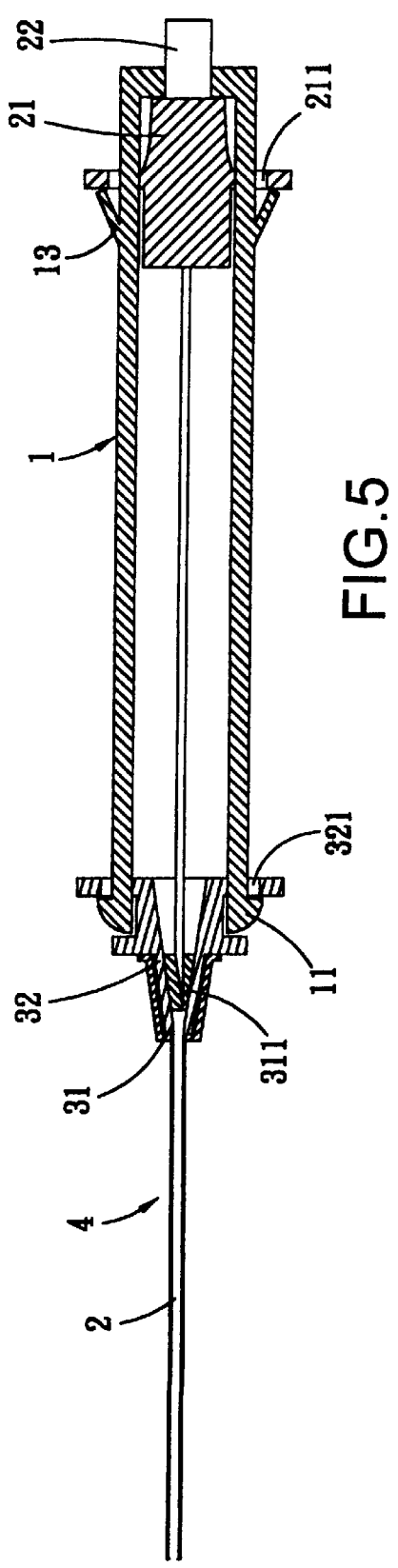

STRUCTURE FOR INFUSION CATHETER NEEDLE

BACKGROUND OF THE INVENTION

1) Field of the Invention

The present invention relates to an improved structure of infusion catheter needle in medical application; and more particularly, to a structure that allows the used steel needle be secured within a needle protection to prevent for the medical personnel from HIV, hepatitis B and C affections due to accidental needlestick injury and a safe disposal of the used steel needle.

2) Description of the Prior Art

Whereas more residual blood stains are found on the used steel needle for intravenous injection due to its comparatively larger inner diameter, and its length also relatively increases the exposure of risks, the chance of accidental needlestick injury to the medical personnel is higher, and in turn the chance of resulted affection is also higher.

However, there are very few safety intravenous catheter needles available in the market. In a prior art of the present invention as illustrated in FIG. 1, a steel needle is inserted in a plastic soft needle 20. Once both needles punctuate into the vein, the steel needle 10 is drawn out and a tube is connected to the plastic soft needle to start intravenous injection. However, once drawn out, the steel needle 10 must be inserted into a casing to prevent accidental needlestick injury to the medical personnel since any such accidental needlestick injury may well cause the medical personnel to be vulnerable to blood affection, namely, HIV, hepatitis B and C. Furthermore, in the subsequent disposal, the steel needle 10 can be easily exposed due to the escaping casing due to impact and compression, threatening the health of those who handle medical refuses.

Safety intravenous catheter needles available in the general market are either complicate in structure thus to increase production cost or too many steps are required in the use as a dedicated before job training is needed thus to increase time cost, or both.

SUMMARY OF THE INVENTION

The primary objective of the present invention is to provide an improved structure of an intravenous catheter needle for protecting medical personnel and those who handle the medical refuses from affections of HIV, hepatitis B and C due to accidental needlestick injury in the course of the disposal of the needle since the used needle can be fully secured in the needle protection.

Another objective of the present invention is to provide an improved structure of an intravenous catheter needle comprised of a plastic soft needle, a needle protection, and a steel protection chute that can lower the production cost of a safety needle.

BRIEF DESCRIPTION OF THE DRAWINGS

FIG. 4 shows a front view of the present invention during injection; and

FIG. 5 shows a front view of the present invention when drawn out.

DETAILED DESCRIPTION OF THE PREFERRED EMBODIMENTS

Figure 1:
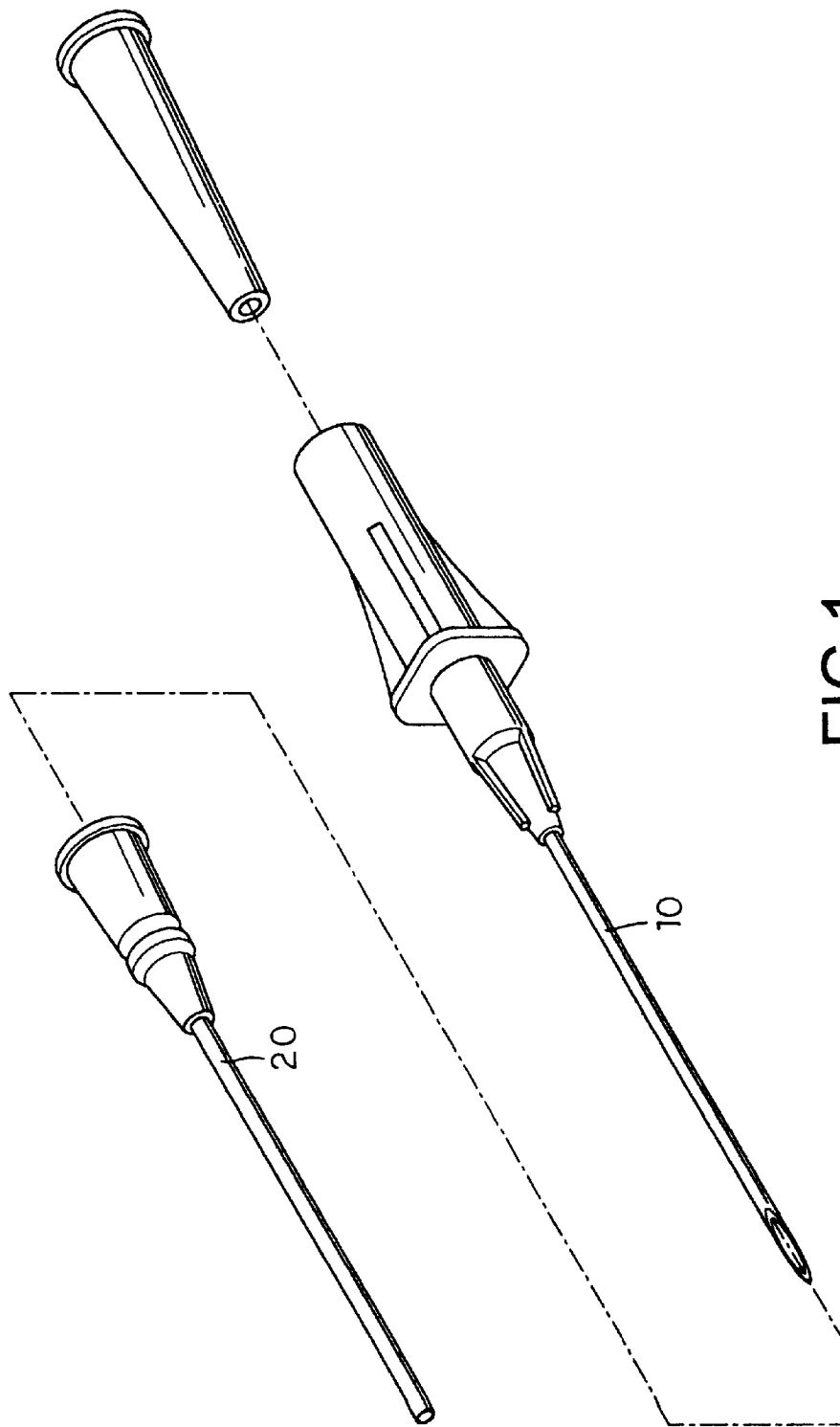
FIG. 1 shows a view of a prior art.
Figure 2:
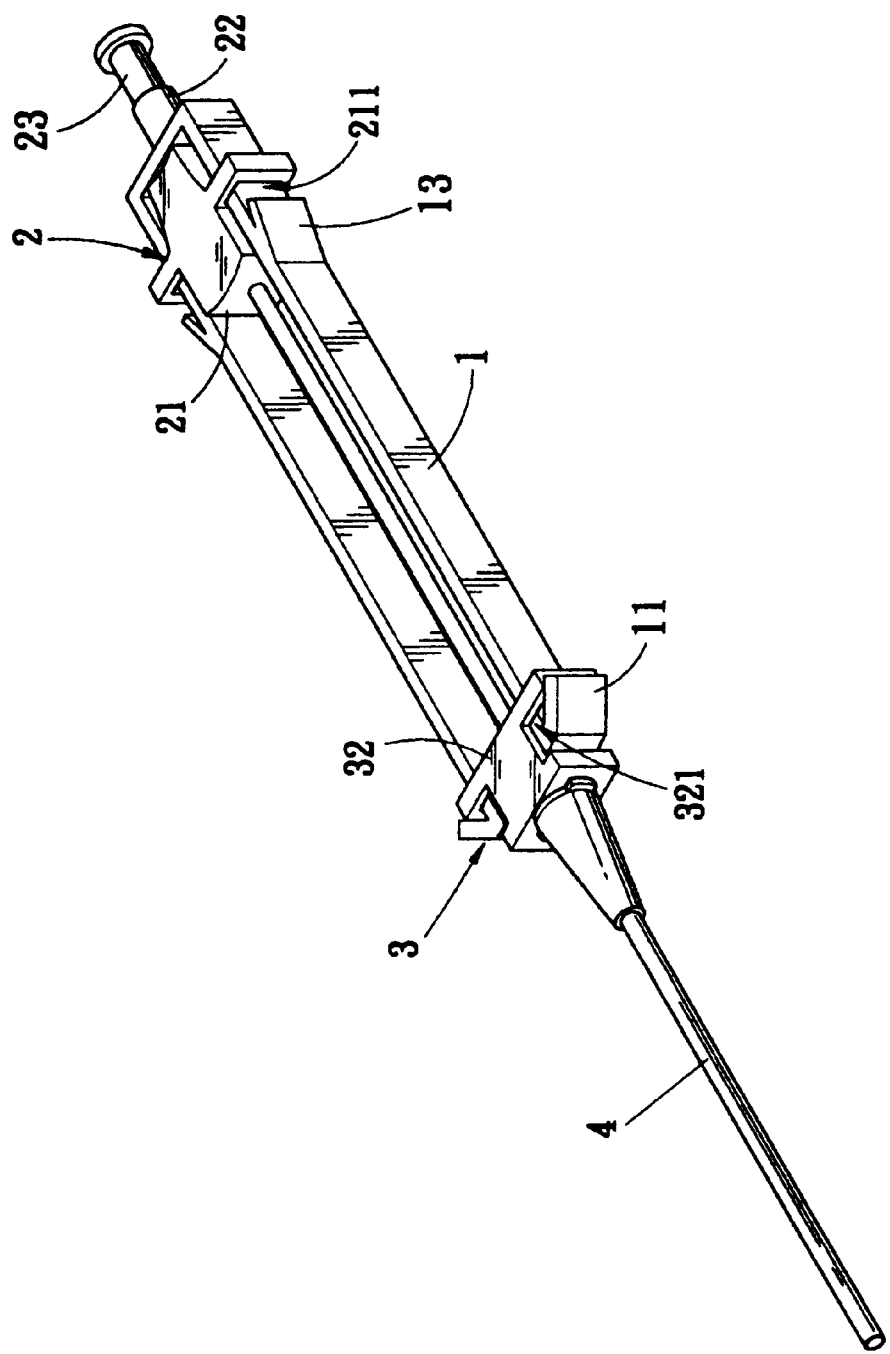
FIG. 2 shows a view of the present invention when assembled.
Figure 3:
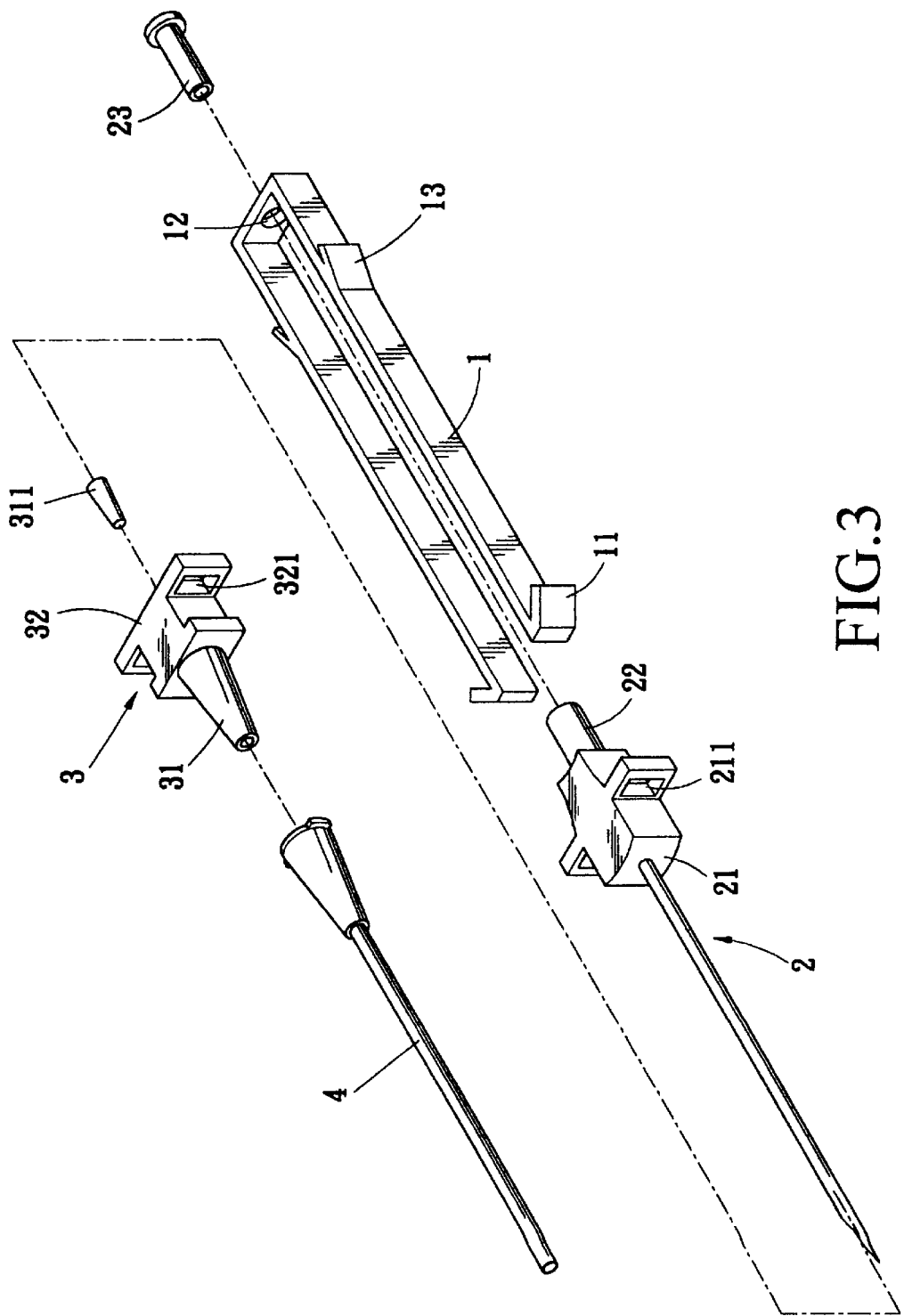
FIG. 3 shows a view of the breakdown of the present invention.

Referring to FIGS. 2 and 3, the present invention is essentially comprised of a steel needle chute 1 which is a long and recessed casing, within, a catch part 11 is provided on the chute 1 and an opening 12 is provided below the chute 1 while a catch 13 is each provided on both sides close to where above the opening 12; a steel needle 2, provided onto a base 21 which is received in the chute 1, a barrel 22 is provided at the bottom of the base 21 to connect a mechanism 23 of blood back-flow and air exchange, and at where corresponding to the opening 12 below the chute 1, an eyelet 211 is each provided on both sides of said base 21 to be inserted into the catch part 11 of the chute 1 so to allow the movement of the base 21 in the chute and the engagement to the catch 13; a needle protection for the insertion by the steel needle 2, one end of the protection 3 is made in a cone shape 31 and a rubber plug 311 is provided at the top of said cone 31, while a joint 32 is provided at the other end of the protection 3, an eyelet 321 is each provided on both sides of said joint 32 to receive the catch 11 of the chute 1 and both eyelets 321 correspond to that from both sides of the base 21; and a plastic soft needle tube 4 to receive the insertion by the cone 31 of the protection 3 and further the insertion by the steel needle 2.

Now referring to FIGS. 4 and 5, the present invention permits the steel 2 when drawn out is at the same time caught and secured within the steel chute 1. While in use, the steel needle 2 with its inclined section facing above to punctuate the skin and enter into the vein of a patient. Then the medical personnel with one hand holding firm the joint 32 of the needle protection and another hand with two fingers holding onto the arc on both sides of the steel needle base 21 to draw back the steel needle 2 to engage the catch 13 provided above the opening 12 below the chute 1; meanwhile, the barrel 22 at the bottom of the base 21 and the blood backflow and air exchange mechanism 23 pass through the opening 12 below the chute 1 while the needle 2 maintains staying within the cone 31 of the protection 3. Consequently, it is not necessary for the steel needle 2 to be recovered or wrapped, instead, it is confined in the rubber plug 311. Accidental needlestick by the used steel needle 2 is prevented for the medical personnel since the residual blood in the needle is stopped from outflow and the safety for those who handle the medical refuses is also warranted.

To sum up, the improved structure of the present invention for the intravenous catheter needle effectively prevent blood affection due to accidental needlestick injury since it is not required to be recovered or wrapped when the needle is used.

What is claimed is:

1. An intravenous catheter needle comprising:
   a) a needle chute having an elongated configuration with two opposite sides, a first catch extending outwardly from each of the two opposite sides at a first end of the needle chute, and a second catch extending outwardly from each of the two opposite sides adjacent to a second end of the needle chute;
   b) a protection member having a joint section with outwardly extending first eyelets engaging the first catches so as to attach the protection member to the first end of the needle chute, the protection member having a hollow cone extending therefrom and a rubber plug located in the hollow case;
   c) a plastic needle tube extending from the hollow cone, the plastic needle tube having a distal end; and, d) a steel needle having a base with second eyelets extending outwardly therefrom slidably engaging the two opposite sides of the needle chute such that the steel needle is movable between a first position, wherein a distal end of the steel needle extends beyond the distal end of the plastic needle, and a second position wherein the distal end of the steel needle is located within the rubber plug, the steel needle being retained in the second position by engagement of the second eyelets with the second catches.

* * * * *